(12) United States Patent
Neumann et al.

(10) Patent No.: US 9,873,612 B2
(45) Date of Patent: Jan. 23, 2018

(54) CATALYTIC FORMATION OF CARBON MONOXIDE (CO) AND HYDROGEN ($H_2$) FROM BIOMASS

(71) Applicant: YEDA RESEARCH AND DEVELOPMENT CO. LTD, Rehovot (IL)

(72) Inventors: Ronny Neumann, Kfar Saba (IL); Bidyut-Bikash Sarma, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 39 days.

(21) Appl. No.: 15/031,749

(22) PCT Filed: Oct. 28, 2014

(86) PCT No.: PCT/IL2014/050933
§ 371 (c)(1),
(2) Date: Apr. 25, 2016

(87) PCT Pub. No.: WO2015/063763
PCT Pub. Date: May 7, 2015

(65) Prior Publication Data
US 2016/0264412 A1    Sep. 15, 2016

Related U.S. Application Data

(60) Provisional application No. 61/896,715, filed on Oct. 29, 2013.

(51) Int. Cl.
*C01B 3/16* (2006.01)
*C10K 3/04* (2006.01)
(Continued)

(52) U.S. Cl.
CPC ............... *C01B 3/16* (2013.01); *B01J 27/199* (2013.01); *C01B 3/02* (2013.01); *C07C 51/235* (2013.01);
(Continued)

(58) Field of Classification Search
CPC ....... C07C 51/235; C07C 53/02; Y02P 30/20; C01B 3/16; C01B 2203/0283; C01B 3/02;
(Continued)

(56) References Cited

U.S. PATENT DOCUMENTS

| | | | |
|---|---|---|---|
| 2010/0324310 A1* | 12/2010 | Dumesic | B01J 35/0006 549/326 |
| 2013/0245319 A1* | 9/2013 | Bosmann | C07C 51/23 562/531 |
| 2015/0152562 A1* | 6/2015 | Bernical | C01B 3/32 205/628 |

FOREIGN PATENT DOCUMENTS

FR    2989366    10/2013

OTHER PUBLICATIONS

Albert, Jakob, et al. "Selective oxidation of complex, water-insoluble biomass to formic acid using additives as reaction accelerators." Energy & Environmental Science 5.7 (2012): 7956-7962.
(Continued)

*Primary Examiner* — Anthony J Zimmer
*Assistant Examiner* — Syed Iqbal
(74) *Attorney, Agent, or Firm* — Mark Cohen; Pearl Cohen Zedek Latzer Baratz LLP

(57) ABSTRACT

The present invention relates to methods of preparing carbon monoxide (CO) and hydrogen ($H_2$) by reacting biomass, a biomass component (e.g., lignin, ligno-cellulose, cellulose, hemiceullose or combination thereof) or a carbohydrate from any source with a polyoxometalate catalyst such as $H_5PV_2Mo_{10}O_{40}$, or solvates thereof, in the presence of a
(Continued)

concentrated acid, under conditions sufficient to yield carbon monoxide (CO); followed by electrochemical release of hydrogen ($H_2$). The carbon monoxide (CO) and hydrogen ($H_2$) may be combined in any desired proportion to yield synthesis gas (Syngas). The present invention further relates to methods for preparing $H_2$, CO and formic acid/formaldehyde from biomass, a biomass component and/or from carbohydrates.

38 Claims, 2 Drawing Sheets

(51) Int. Cl.
| | |
|---|---|
| C10G 1/06 | (2006.01) |
| C10G 3/00 | (2006.01) |
| C25B 1/00 | (2006.01) |
| C25B 1/02 | (2006.01) |
| B01J 27/199 | (2006.01) |
| C01B 3/02 | (2006.01) |
| C07C 51/235 | (2006.01) |
| C10K 3/06 | (2006.01) |

(52) U.S. Cl.
CPC .............. *C10G 1/065* (2013.01); *C10G 3/44* (2013.01); *C10K 3/04* (2013.01); *C10K 3/06* (2013.01); *C25B 1/00* (2013.01); *C25B 1/02* (2013.01); *C01B 2203/0283* (2013.01); *C01B 2203/1041* (2013.01); *Y02E 60/366* (2013.01); *Y02P 30/20* (2015.11)

(58) Field of Classification Search
CPC .. C01B 2203/1041; B01J 27/199; C10G 3/44; C10G 1/065; C10K 3/06; C10K 3/04; C25B 1/02; C25B 1/00
See application file for complete search history.

(56) References Cited

OTHER PUBLICATIONS

Binder, Joseph B., and Ronald T. Raines. "Simple chemical transformation of lignocellulosic biomass into furans for fuels and chemicals." Journal of the American Chemical Society 131.5 (2009): 1979-1985.
Chheda, Juben N., et al. "Liquid-phase catalytic processing of biomass-derived oxygenated hydrocarbons to fuels and chemicals." Angewandte Chemie International Edition 46.38 (2007): 7164-7183.
Dhar, H. P., L. G. Christner, and A. K. Kush. "Nature of CO adsorption during H 2 oxidation in relation to modeling for CO poisoning of a fuel cell anode." Journal of the Electrochemical Society 134.12 (1987): 3021-3026.
Efremenko, Irena, and Ronny Neumann. "Computational insight into the initial steps of the Mars—van Krevelen mechanism: electron transfer and surface defects in the reduction of polyoxometalates." Journal of the American Chemical Society 134.51 (2012): 20669-20680.
Fellay, Céline, et al. "A Viable Hydrogen-Storage System Based on Selective Formic Acid Decomposition with a Ruthenium Catalyst." Angewandte Chemie 120.21 (2008): 4030-4032.

Huber, George W., et al. "Raney Ni—Sn catalyst for H2 production from biomass-derived hydrocarbons." Science 300.5628 (2003): 2075-2077.
Huber, George W., et al. "Production of liquid alkanes by aqueous-phase processing of biomass-derived carbohydrates." Science 308.5727 (2005): 1446-1450.
Huber, George W., et al. "Synthesis of transportation fuels from biomass: chemistry, catalysts, and engineering." Chemical reviews 106.9 (2006): 4044-4098.
Khenkin, Alexander M., and Ronny Neumann. "Oxidative C—C Bond Cleavage of Primary Alcohols and Vicinal Diols Catalyzed by H5PV2Mo10O40 by an Electron Transfer and Oxygen Transfer Reaction Mechanism." Journal of the American Chemical Society 130.44 (2008): 14474-14476.
Kim, Won Bae, et al. "Powering fuel cells with CO via aqueous polyoxometalates and gold catalysts." Science 305.5688 (2004): 1280-1283.
Kunkes, Edward L., et al. "Catalytic conversion of biomass to monofunctional hydrocarbons and targeted liquid-fuel classes." Science 322.5900 (2008): 417-421.
Li, Jiang, et al. "Catalytic Air Oxidation of Biomass-Derived Carbohydrates to Formic Acid." ChemSusChem 5.7 (2012): 1313-1318.
Matson, Theodore D., et al. "One-pot catalytic conversion of cellulose and of woody biomass solids to liquid fuels." Journal of the American Chemical Society 133.35 (2011): 14090-14097.
Melero, Juan Antonio, et al. "Biomass as renewable feedstock in standard refinery units. Feasibility, opportunities and challenges." Energy & environmental science 5.6 (2012): 7393-7420.
Neumann, Ronny. "Activation of molecular oxygen, polyoxemetalates, and liquid-phase catalytic oxidation," Inorganic chemistry 49.8 (2010): 3594-3601.
Newsome, David S. "The water-gas shift reaction." Catalysis Reviews Science and Engineering 21.2 (1980): 275-318.
Stiles, Alvin B. "Methanol, past, present, and speculation on the future." AIChE Journal 23.3 (1977): 362-375.
Sutton, Andrew D., et al. "The hydrodeoxygenation of bioderived furans into alkanes." Nature chemistry 5.5 (2013): 428-432.
Trillo, J. M., G. Munuera, and J. M. Criado. "Catalytic decomposition of formic acid on metal oxides." Catalysis Reviews 7.1 (1972): 51-86.
Tsigdinos, George A., and Calvin J. Hallada. "Molybdovanadophosphoric acids and their salts. I. Investigation of methods of preparation and characterization." Inorganic Chemistry 7.3 (1968): 437-441.
Wang, Zhi-Li, et al. "An efficient CoAuPd/C catalyst for hydrogen generation from formic acid at room temperature." Angewandte Chemie International Edition 52.16 (2013): 4406-4409.
Weinstock, Ira A., et al. "A new environmentally benign technology for transforming wood pulp into paper. Engineering polyoxometalates as catalysts for multiple processes." Journal of Molecular Catalysis A: Chemical 116.1-2 (1997): 59-84.
Wölfel, Rene, et al. "Selective catalytic conversion of biobased carbohydrates to formic acid using molecular oxygen." Green Chemistry 13.10 (2011): 2759-2763.
Zhou, Chun-Hui, et al. "Catalytic conversion of lignocellulosic biomass to fine chemicals and fuels." Chemical Society Reviews 40.11 (2011): 5588-5617.
Zhu, Li, et al. "Structural features affecting biomass enzymatic digestibility." Bioresource Technology 99.9 (2008): 3817-3828.

\* cited by examiner

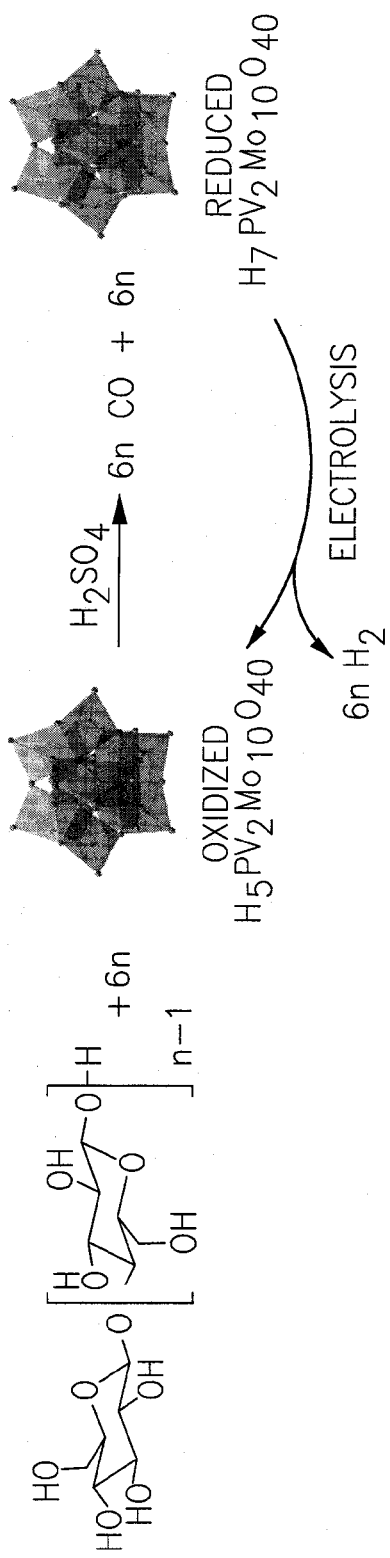
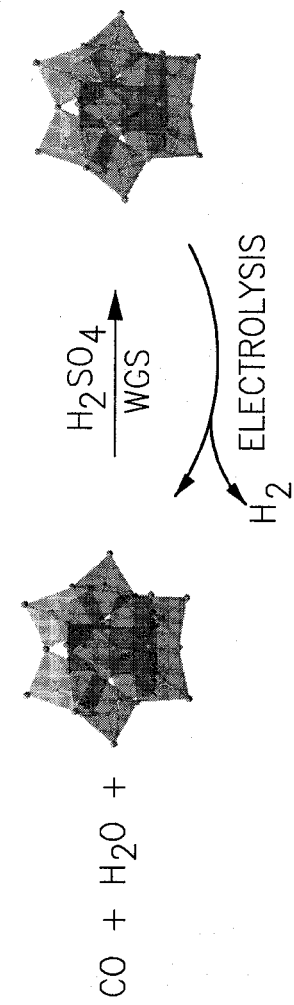
Figure 2A
Figure 2B

CATALYTIC FORMATION OF CARBON MONOXIDE (CO) AND HYDROGEN ($H_2$) FROM BIOMASS

CROSS-REFERENCE TO RELATED APPLICATIONS

This application is a National Phase Application of PCT International Application No. PCT/IL2014/050933, International Filing Date 28 Oct., 2014, claiming priority from United States Provisional Ser. No. 61/896,715 Patent Application, which is hereby incorporated by reference.

FIELD OF THE INVENTION

The present invention relates to methods of preparing carbon monoxide (CO) and hydrogen ($H_2$) by reacting biomass, a biomass component (e.g., lignin, ligno-cellulose, cellulose, hemiceullose or combination thereof) or a carbohydrate from any source with a polyoxometalate catalyst such as $H_5PV_2Mo_{10}O_{40}$, or solvates thereof, in the presence of a concentrated acid, to yield carbon monoxide (CO); followed by electrochemical release of hydrogen ($H_2$). The carbon monoxide (CO) and hydrogen ($H_2$) may be combined in any desired proportion to yield synthesis gas (Syngas). The present invention further relates to methods for preparing $H_2$, CO and formic acid/formaldehyde from biomass, a biomass component and/or from carbohydrates.

BACKGROUND OF THE INVENTION

Environmental concerns and decreasing amounts of fossil fuels, especially oil, requires the development of renewable resources for liquid fuels, which are critical for transportation and industrial sectors. Solar energy and solar fuels have been touted as the ultimate, indefatigable sources of energy, but the storage of sunlight and its use in a practical way remains a major challenge of modern times.

Biomass has potential as a renewable resource and solar-based fuel where the conversion of water and carbon dioxide to glucose and then to other organic materials is achieved by photosynthesis followed by further biosynthetic pathways. Thus, the storage of solar energy in terrestrial biomass takes advantage of natural photosynthetic pathways and further biosynthetic reactions using $CO_2$ and $H_2O$ as carbon and hydrogen atom sources. Terrestrial plants contain hemicellulose, ~$(C_5H_{10}O_5)_n$, and cellulose, $(C_6H_{12}O_6)_n$, that can be re-processed to obtain a convenient hydrocarbon fuel. Typically, biomass contains 35-50% cellulose, 20-35% hemicellulose, and 10-25% lignin. Biorefining of biomass is an emerging field, and processes including catalytic hydrolysis, solvolysis, liquefaction, pyrolysis, gasification, hydrogenolysis and hydrogenation are all being considered.(1,2) The transformation of cellulose to D-glucose, its sole component, and then to ethanol to be used as a biofuel by fermentation is perhaps the most developed technology, however the failure of simple acids to hydrolyze cellulose selectively (3) remains a problem that requires the use of more expensive cellusomes.(4) The hydrolysis/fermentation approach also has the disadvantage that hemicellulose and its major hydrolysis product, D-xylose, still cannot be used to form ethanol. On the other hand, cellulose/hemicellulose hydrolysis has been suggested as a route to chemicals such as sugars, formic acid, levulinic acid and hydroxymethyl-furfuraldehyde among others.(5,6) Other efforts have been made to convert cellulose or cellulose derived materials to hydrocarbons,(7-9), hydrogen,(10,11), and furans.(12) Despite the aforementioned advances, reaction selectivity is typically low and process schemes are quite complicated.

Synthesis gas (also known as Syngas), is a fuel gas mixture consisting primarily of hydrogen ($H_2$), carbon monoxide (CO), and often some carbon dioxide ($CO_2$). Synthesis gas is a known industrial commodity that is used an intermediary building block for the production of various fuels such as synthetic natural gas, ammonia, methanol, and synthetic petroleum fuel. For example, hydrocarbons can be prepared from synthesis gas via the Fischer-Tropsch process (13), or methanol can be synthesized both as a fuel and fuel precursor. (14) Synthesis gas may also be used as a direct fuel source. In a purified state, the hydrogen component of synthesis gas can also be used to directly power hydrogen fuel cells for electricity generation and fuel cell electric vehicle propulsion. Hydrogen can also be used to prepare ammonia by the Haber-Bosch process.

It has previously been shown by Khenkin et al., that a phosphovanadomolybdic acid such as the $H_5PV_2Mo_{10}O_{40}$ polyoxometalate catalyzes the carbon-carbon bond cleavage of vicinal diols and primary alcohols.(15) In this electron transfer-oxygen transfer type reaction, oxygen atoms from the polyoxometalate are inserted into the carbon-carbon bond and the hydrogen atoms released are retained on the polyoxometalate as protons and electrons. For example, the initial product of ethylene glycol oxidation was formaldehyde and 1-butanol oxidation initially yielded formaldehyde and propionaldehyde. Wasserscheid et al. showed that $H_5PV_2Mo_{10}O_{40}$ can convert carbohydrates such as hemicellulose in water under rather high $O_2$ pressures (30 bar) to formic acid in a 50% yield with co-formation of 50% $CO_2$, but cellulose reacted in only low yields.(16,17) Vanadium oxide was similarly reactive in this reaction.(18) Analysis of the results shows that the maximum yield of formic acid is around 50% for hemicellulose and around only 7% for cellulose.(16-18) It was suggested (16-18) that formic acid could be further transformed to $H_2$ and $CO_2$, typically over a noble metal catalyst as previously described.(19,20) Alternatively, acid catalyzed dehydration of formic acid to CO and $H_2O$ can be contemplated.(21) Using D-glucose as a model, this translates into a potential yield, at the observed 50% yield of formic acid, of 3 mol of $H_2$ or CO but not both per mol D-glucose. This is far from the optimum of 6 mol of both CO and $H_2$ per mol D-glucose.

U.S. Patent Application No. US 2013/0245319 discloses a method for catalytically producing formic acid, by reacting an alpha-hydroxyaldehyde, alpha-hydroxycarboxylic acid, a carbohydrate or a glycoside with a polyoxometallate ion catalyst, of the general formula $[PMo_xV_yO_{40}]^{q-}$, using water as a solvent.

Weinstock, I. A. et at (26) describes the use of Keggin-type polyoxometalate (POM) salts and oxygen to bleach wood pulp for use in the manufacture of paper.

U.S. Pat. Nos. 5,302,248, 5,549,789 and 5,695,606 describe a method for delignifying/bleaching wood pulp for the manufacture of paper. The bleaching process involves exposing the wood pulp to a polyoxometalate of the formula $[V_1\text{-}Mo_mW_nNb_oTa_p(TM)_qX_rO_s]^{x-}$, to produce water soluble oxidized lignin, which is then oxidatively degraded to $CO_2$ by heating the solution to high temperatures.

Synthesis gas is an important commodity used for formation of fuel and fuel precursors, among other industrial applications. There remains an unmet need for efficient methods for preparing synthesis gas from biomass.

SUMMARY OF THE INVENTION

The present invention relates to a method of preparing carbon monoxide (CO) and hydrogen ($H_2$) by reacting biomass, a biomass component (e.g., lignin, ligno-cellulose, cellulose, hemiceullose or combination thereof) or a carbohydrate from any source with a polyoxometalate catalyst in the presence of a concentrated acid under conditions sufficient to yield carbon monoxide (CO); followed by electrochemical release of hydrogen ($H_2$). The carbon monoxide (CO) and hydrogen ($H_2$) may be combined in any desired proportion to yield synthesis gas (Syngas). The present invention further relates to a method for preparing CO by reacting biomass, a biomass component and/or a carbohydrate with a polyoxometalate catalyst in the presence of a concentrated acid, under conditions sufficient to yield carbon monoxide (CO). Carbon dioxide ($CO_2$) may optionally form in this process. The present invention further relates to a method for preparing hydrogen ($H_2$) by a water gas shift reaction involving reacting biomass, a biomass component or a carbohydrate from any source with a polyoxometalate catalyst in the presence of a concentrated acid, under conditions sufficient to yield carbon dioxide ($CO_2$); followed by electrochemical release of hydrogen ($H_2$). The present invention further relates to a method for preparing formic acid, by contacting a carbohydrate with a polyoxometalate catalyst in a solvent selected from an alcohol or a mixture of alcohol and water, under conditions sufficient to yield formic acid. The polyoxometalate catalyst may be, e.g., $H_5PV_2Mo_{10}O_{40}$, or solvates or hydrates thereof, or any additional polyoxometalate catalysts described herein.

Terrestrial plants contain 70% hemicellulose and cellulose that are a significant renewable bioresource with potential as an alternative to petroleum feedstock for carbon-based fuels. The efficient and selective deconstruction of carbohydrates to their basic components, carbon monoxide and hydrogen, so called synthesis gas, is an important key step towards the realization of this potential, because the formation of liquid hydrocarbon fuels from synthesis gas are known technologies. The present invention demonstrates for the first time that by using a polyoxometalate as an electron transfer-oxygen transfer catalyst, carbon monoxide is formed by cleavage of all the carbon-carbon bonds through dehydration of initially formed formic acid. In this oxidation-reduction reaction, the hydrogen atoms are stored on the polyoxometalate as protons and electrons, and can be electrochemically released from the polyoxometalate as hydrogen. Together, synthesis gas is formed. In a hydrogen economy scenario, this method can also be used to convert carbon monoxide to hydrogen. Furthermore, this method is not limited to carbohydrates, and also applicable to other biomass components such as lignin and ligno-cellulose, as well as to biomass as a whole or any portion thereof.

Advantageously, in the aforementioned processes, the polyoxometalate solution can be reused without need for any catalyst recovery procedures. Thus, if desired, the reaction may be repeated for at least one additional cycle (e.g., 10 or more cycles), without the need to recycle or recover the solvent. However, if desired, the polyoxometalate may be subject to recovery/recycling methods as known in the art.

The present invention is based on the unexpected finding that polyoxometalate catalysts such as $H_5PV_2Mo_{10}O_{40}$ catalyse the efficient, two-step, one pot conversion of biomass or a component of biomass or carbohydrates from any source, including but not limited to biomass-derived lignin, cellulose and hemicellulose polysaccharides, $(C_nH_{2n}O_n)_m$ where n=6 for D-glucose and n=5 for D-xylose, to carbon monoxide (CO) and hydrogen ($H_2$) with high selectivity and efficiency, at mild conditions. Advantageously, the CO and $H_2$ may be combined in any desired proportion to yield synthesis gas (Syngas). As demonstrated herein, using a vanadium containing polyoxometalate, $H_5PV_2Mo_{10}O_{40}$, as catalyst in sulfuric acid as solvent, biomass from various sources, as well as its individual components lignin, hemicellulose and cellulose were oxidized to carbon monoxide (CO), where the hydrogen atoms were stored on the polyoxometalates as protons and electrons. Hydrogen gas ($H_2$) was electrochemically released from the polyoxometalate, which returns to its original oxidized state. In this way, biomass, lignin, cellulose and hemicellulose were quantitatively converted to synthesis gas, CO and $H_2$, which can be reacted to yield hydrocarbons by known technologies. In another embodiment, CO was oxidized in situ to yield $CO_2$ and $H_2$ via a type of water gas shift reaction.

As contemplated herein, the inventors have found that reacting biomass or components of biomass with a concentrated acid in the presence of a polyoxometalate catalyst leads to the formation of carbon monoxide (CO), in some cases through intermediate formation of formic acid (HC(=O)OH) and formaldehyde (HC(=O)H). Transformation of formic acid/formaldehyde to CO requires the presence of a concentrated acid, i.e., the concentration of the acid is preferably about 80 w/w % in water or higher. In one preferred embodiment, the reaction is performed in neat acid, wherein the acid is used as a solvent for the reaction. Hydrogen ($H_2$) may further be generated electrochemically. Combining the products of each step (i.e., CO and $H_2$) generates Syngas as an end product. The two steps process (formation of CO followed by $H_2$), may advantageously be performed simultaneously in one pot, or sequentially.

For production of Syngas, formic acid or CO, the reaction may be conducted in the absence of oxygen (anaerobic) or presence of oxygen (aerobic) conditions. Each possibility represents a separate embodiment of the present invention.

Thus, in one embodiment, the present invention provides a method for preparing carbon monoxide (CO) and hydrogen ($H_2$) from biomass or a component thereof, or from a carbohydrate, the method comprising the steps of (a) contacting the biomass, biomass component or carbohydrate with a polyoxometalate catalyst or a solvate thereof in the presence of a concentrated acid under conditions sufficient to produce carbon monoxide (CO) and optionally carbon dioxide ($CO_2$); and (b) electrochemically producing hydrogen ($H_2$). The reaction may be carried out under aerobic or anaerobic conditions. Steps (a) and (b) may be performed simultaneously, in one pot, or alternatively these steps may be performed sequentially where step (b) follows step (a). Each possibility represents a separate embodiment of the present invention.

In some embodiments, the method further comprises combining the carbon monoxide (CO) produced in step (a) or a portion thereof, and the hydrogen ($H_2$) produced in step (b) or a portion thereof, so as to form synthesis gas (Syngas).

Fast removal of the CO formed by purging the reaction mixture can prevent its further oxidation to $CO_2$. Thus, in some embodiments, the method further comprises the step of removing CO from the reaction after step (a), for example by purging.

In another embodiment, the present invention relates to method for preparing carbon monoxide (CO) and optionally carbon dioxide ($CO_2$) from biomass or a component thereof, or from a carbohydrate, the method comprising the step of contacting the biomass, biomass component or carbohydrate with a polyoxometalate catalyst or a solvate thereof, in the presence of a concentrated acid under conditions sufficient to produce carbon monoxide (CO) and optionally carbon dioxide ($CO_2$). The reaction may be carried out under aerobic or anaerobic conditions. Each possibility represents a separate embodiment of the present invention.

In some embodiments, method of the invention comprises the use of whole biomass, which comprises primarily lignin, ligno-cellulose, cellulose and hemi-cellulose. In other embodiments, the method of the invention comprises the use of biomass component selected from lignin, ligno-cellulose, cellulose, hemi-cellulose, and any combination thereof. Each possibility represents a separate embodiment of the present invention.

In some embodiments, the biomass may be separated into one or more of its components prior to performing the method of the invention. In some embodiments, the biomass is separated into hemicellulose and ligno-cellulose, and ligno-cellulose is used in the method of the invention. Alternatively, the biomass may be separated into hemicellulose and ligno-cellulose, the ligno-cellulose further separated into lignin and cellulose, and either lignin or cellulose is used in the method of the invention. Each possibility represents a separate embodiment of the present invention.

In other embodiments, the method of the invention comprises the use of a carbohydrate. Any source of carbohydrate can be used for the process of the present invention. Non-limiting examples include monosaccharides, disaccharides, trisaccharides, oligosaccharides, polysaccharides, sugar alcohols, plant biomass, starch and any combination thereof. In some embodiments, the carbohydrate is derived from terrestrial biomass, i.e. cellulose, hemicellulose or a combination thereof.

The acid is preferably used at a concentration of greater than about 50%, preferably greater than about 80%, more preferably greater than about 90%, more preferably neat acid (about 98%), used as a solvent for the reaction. Suitable acids for use in the process of the invention include, but are not limited to, $H_2SO_4$, $HClO_4$, $H_3PO_4$, $CH_3SO_3H$, $CF_3SO_3H$, $CF_3COOH$, $CH_3COOH/H_2SO_4$, and any combination thereof. Each possibility represents a separate embodiment of the present invention. The use of concentrated $H_2SO_4$, i.e., about 85% w/w in water or greater, e.g., approximately 98 w/w % in water $H_2SO_4$, is currently preferred.

In some embodiments, step (b) of the process, i.e., electrochemical generation of $H_2$, is conducted using an electrode selected from a Au, Ag, Ni, Co, Pt, Pd, Cu, Al, Au/Ag, Au/Cu, Au/Ag/Cu, Au/Pt, Au/Pd, Au/Ag/Cu/Pd, Pt—Rh, Ni—Co, and Pt—Ni—Fe electrode. Use of a Pt gauze electrode is currently preferred.

In another aspect, the present invention is based on the discovery of an improved process for preparing formic acid from carbohydrates. The conversion to biomass to formic acid has previously been described by other (US 2013/0245319, (16)), using water as a reaction solvent. It has now been expectedly been discovered that the use of an alcohol as a reaction solvent, with or without water, significantly increases the yield of the reaction. Thus, in another embodiment, the present invention relates to a method for preparing formic acid from a carbohydrate, the method comprising the step of contacting the carbohydrate with a polyoxometalate catalyst or a solvate thereof, in a solvent selected from an alcohol or a mixture of alcohol and water under conditions sufficient to produce formic acid. The alcohol is preferably methanol, but can also be a C2-C4 alcohol. Any of the carbohydrates described herein can be used for this reaction. The reaction may be conducted under aerobic or anaerobic conditions. Each possibility represents a separate embodiment of the present invention.

In another aspect, the methods of the present invention may be used to produce Hydrogen ($H_2$) via a water gas shift reaction. It has been discovered that CO is partially oxidized to $CO_2$ during transformation of biomass. Thus, in some embodiments, the process may be carried out to effectuate complete conversion of CO to $CO_2$, followed by electrochemical release of hydrogen as described above, so as to complete a water gas shift reaction. Thus, in another aspect, the present invention relates to a method for preparing hydrogen ($H_2$) from biomass or a component thereof, or from a carbohydrate, the method comprising the steps of (a) contacting the biomass, biomass component or carbohydrate with a polyoxometalate catalyst or a solvate thereof in the presence of a concentrated acid under conditions sufficient to produce carbon dioxide ($CO_2$); and (b) electrochemically producing hydrogen ($H_2$); wherein steps (a) and (b) are performed simultaneously or sequentially. Any of the reaction conditions described above, including the type of biomass, acid, etc. may be used for this process. Each possibility represents a separate embodiment of the present invention.

Polyoxometalate catalysts suitable for use in the present invention are typically polyoxoanion salt represented by the general formula $[X_xM_mO_y]^{q-}$ or a solvate thereof, wherein X is a metal or non-metal heteroatom, or a proton; M are addenda atoms selected from the group consisting of tungsten (W), molybdenum (Mo), niobium (Nb), vanadium (V), tantalum (Ta), bismuth (Bi), antimony (Sb), tin (Sn) and any combination thereof; O is oxygen; x is an integer between 0 and 6; m is an integer between 4 and 200; y is an integer between 5 and 1000; and q is an integer between 0 and 30. Non-limiting examples of such catalysts are provided hereinbelow. In a currently preferred embodiment, the polyoxometalate catalyst is $H_5PV_2Mo_{10}O_{40}$. Also, polyoxometalate catalysts are often in solvated forms, for example hydrates. Thus, the present invention encompasses the use of polyoxometalate solvates, such as but not limited to polyoxometalate hydrates. Other suitable polyoxometalate solvates are described in the detailed description hereinbelow.

BRIEF DESCRIPTION OF THE DRAWINGS

The present invention will be understood and appreciated more fully from the following detailed description taken in conjunction with the appended figure:

FIG. 1. Cyclic voltammogram of the reaction solution (0.42 M $H_5PV_2Mo_{10}O_{40}$ in $H_2SO_4$). Pt was used as the reference, working and counter electrode, scan rate-200 mV/sec.

FIG. 2. Conversion of cellulose. The conversion of cellulose to CO and $H_2$ (FIG. 2A) and the water gas shift of CO (FIG. 2B).

DETAILED DESCRIPTION OF THE PRESENT INVENTION

Figure 1A:
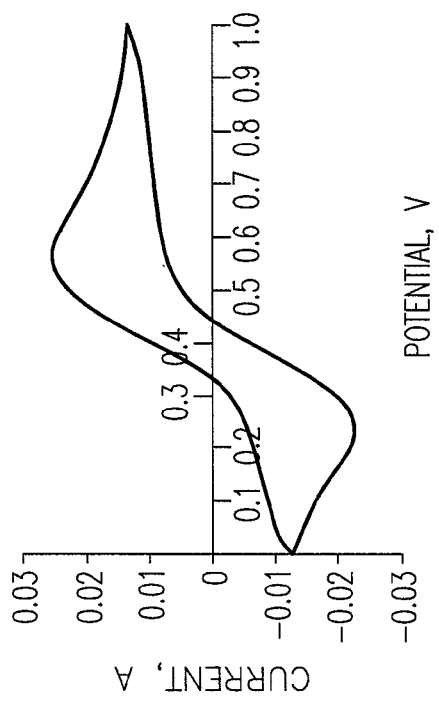
FIG. 1A—at the end of cellulose oxidation, that is 2.7 electrons/$H_5PV_2Mo_{10}O_{40}$.

The present invention serves as a foundation for a new technology for the formation of carbon monoxide (CO) and hydrogen ($H_2$) from biomass or a component thereof, or from a carbohydrate from any source. The two gases which are formed separately can be combined in any desired proportion to yield synthesis gas (Syngas). The present invention further relates to a method for preparing carbon monoxide (CO) from biomass or a component thereof, or from a carbohydrate from any source. The present invention further relates to a method for preparing hydrogen ($H_2$) from biomass or a component thereof, or from a carbohydrate from any source via a water gas shift reaction. The present invention further relates to a method for preparing formic acid from a carbohydrate in a solvent selected from an alcohol or a mixture of alcohol and water.

Purported advantages of these concepts are: (1) as solar energy and other sources (wind, geothermal and nuclear) are more simply transformed to electric power compared with their storage as a chemical fuel, the low-temperature electrochemical approach presented herein has the potential for considerable total energy saving. (2) The synthesis gas yield can be significantly higher than what can be obtained with high-temperature steam reforming of biomass where the need to use $O_2$ from air leads to formation of $CO_2$ as the major product, which is not compensated by $H_2$ formation, and which requires noble metal-based catalysts for quantitative conversions. (3) The concept presented herein indicates a requirement of 1 mole equivalent of polyoxometalate per carbon atom; for example, 10 mg of cellulose per 780 mg polyoxometalate in a one-pot reaction. However, as the substrate conversion is quantitative, all the products are gaseous and the catalyst is very stable under reaction conditions, the present method is applicable to industrial use involving continuous reaction mode in which the substrate can be continuously fed and the resulting gas (CO and/or $H_2$) can be removed continuously using a fixed amount of catalyst.

Definitions

The term "synthesis gas" or "Syngas" is a mixture consisting primarily of hydrogen ($H_2$), carbon monoxide (CO), and optionally some carbon dioxide ($CO_2$).

The term "concentrated acid" refers to an acid that is present at a concentration of about 50% or greater, preferably greater than about 80%, more preferably greater than about 85%, more preferably greater than about 90%, most preferably greater than about 95%. The acid acts as the solvent for the reaction. All percentages described herein refer to weight/weight (w/w) % in water.

Conversion of Biomass Carbohydrates to Formic Acid, Formaldehyde, CO, $H_2$ and Synthesis Gas In one embodiment, the present invention provides method for preparing carbon monoxide (CO) and hydrogen ($H_2$) from biomass, the method comprising the steps of (a) contacting the biomass with a polyoxometalate catalyst or a solvate thereof in the presence of a concentrated acid under conditions sufficient to produce carbon monoxide (CO) and optionally carbon dioxide ($CO_2$); and (b) electrochemically producing hydrogen ($H_2$).

In another embodiment, the present invention provides method for preparing carbon monoxide (CO) and hydrogen ($H_2$) from a biomass component selected from the group consisting of lignin, ligno-cellulose, cellulose, hemicellulose and any combination thereof, the method comprising the steps of (a) contacting the biomass component or combination of components with a polyoxometalate catalyst or a solvate thereof in the presence of a concentrated acid under conditions sufficient to produce carbon monoxide (CO) and optionally carbon dioxide ($CO_2$); and (b) electrochemically producing hydrogen ($H_2$). In one embodiment, the biomass component is cellulose. In another embodiment, the biomass component is hemicellulose. In another embodiment, the biomass component is lignin. In another embodiment, the biomass component is ligno-cellulose. In another embodiment, the biomass component is any combination of cellulose, hemicellulose, lignin and ligno-cellulose. The biomass component may in some embodiments be isolated from whole biomass, or it may be obtained from other sources, for example synthetic or commercial sources.

In another embodiment, the present invention provides method for preparing carbon monoxide (CO) and hydrogen ($H_2$) from a carbohydrate, the method comprising the steps of (a) contacting the carbohydrate with a polyoxometalate catalyst or a solvate thereof in the presence of a concentrated acid under conditions sufficient to produce carbon monoxide (CO) and optionally carbon dioxide ($CO_2$); and (b) electrochemically producing hydrogen ($H_2$).

In each of the aforementioned embodiments, the carbon monoxide (CO) and hydrogen ($H_2$) may be combined in any desired proportion to yield synthesis gas (Syngas).

In each of the aforementioned embodiments, steps (a) and (b) may be performed simultaneously, in one pot, or alternatively these steps may be performed sequentially where step (b) follows step (a). The reaction may be carried out under aerobic or anaerobic conditions. Each possibility represents a separate embodiment of the present invention.

The present invention also may be used to form carbon monoxide (CO) independently of formation of hydrogen ($H_2$), by performing step (a) of the claimed process, and isolating carbon monoxide (CO). Thus, in one embodiment, the present invention relates to a method for preparing carbon monoxide (CO) from biomass, the method comprising the step of contacting the biomass with a polyoxometalate catalyst or a solvate thereof, in the presence of a concentrated acid under conditions sufficient to produce carbon monoxide (CO).

In another embodiment, the present invention relates to a method for preparing carbon monoxide (CO) from a biomass component selected from the group consisting of lignin, ligno-cellulose, cellulose, hemicellulose and any combination thereof, the method comprising the step of contacting the biomass component or combination of components with a polyoxometalate catalyst or a solvate thereof, in the presence of a concentrated acid under conditions sufficient to produce carbon monoxide (CO).

In another embodiment, the present invention relates to a method for preparing carbon monoxide (CO) from a carbohydrate, the method comprising the step of contacting the carbohydrate with a polyoxometalate catalyst or a solvate thereof, in the presence of a concentrated acid under conditions sufficient to produce carbon monoxide (CO).

In each of the aforementioned embodiments, the reaction may be carried out under aerobic or anaerobic conditions. Each possibility represents a separate embodiment of the present invention.

In yet another embodiment, the present invention relates to a method for preparing formic acid from a carbohydrate, the method comprising the step of contacting the carbohydrate with a polyoxometalate catalyst or a solvate thereof, in a solvent selected from an alcohol or a mixture of alcohol and water, under conditions sufficient to produce formic acid.

The ratio of polyoxometalate to biomass may vary from about 0.01 to 10 equivalents of polyoxometalate per carbon atom in the substrate, depending on the nature of the catalyst and substrate. For the production of CO, Syngas or formic acid, the ratio of polyoxometalate to carbohydrate, biomass or biomass component is preferably about 1 equivalent or less of polyoxometalate per carbon atom in the carbohydrate, biomass or biomass component. In some embodiments, the ratio of polyoxometalate to carbohydrate, biomass or biomass component is between about 0.1-1 equivalents of polyoxometalate per carbon atom in the carbohydrate, biomass or biomass component. In other embodiments, the ratio of polyoxometalate to carbohydrate, biomass or biomass component is about 0.1 equivalent of polyoxometalate per carbon atom in the carbohydrate, biomass or biomass component. In other embodiments, the ratio of polyoxometalate to carbohydrate, biomass or biomass component is about 0.5 equivalent of polyoxometalate per carbon atom in the carbohydrate, biomass or biomass component. The aforementioned conditions preferred for the formation of CO, Syngas or formic acid in accordance with some embodiments of the present invention.

Without wishing to be bound by any particular theory and mechanism of action, in the case of carbohydrates, it is contemplated that the process of the invention is effectuated by initially converting the carbohydrate to formaldehyde and formic acid and related hemiacetals/acetals if an alcohol is used as a reaction solvent. The presence of an acid further results in formation of CO, and finally, $H_2$ is electrochemically generated by using, e.g., a Pt electrode. The process is exemplified below in Scheme 1 with respect to glucose, but may be applied to any simple or complex carbohydrates, including cellulose/hemicellulose derived from terrestrial biomass.

Scheme 1

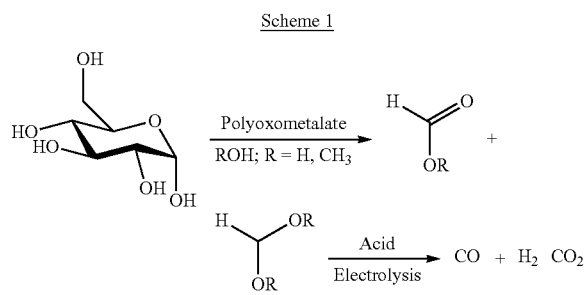

A representation of the transformation of cellulose and hemicellulose using cellulose as a representative substrate is presented in FIG. 2A, wherein the electron transfer-oxygen transfer oxidation of the carbohydrate is shown along with the electrochemical oxidation of the electrons and protons initially stored on the polyoxometalate.

Any concentrated acid can be used in the process of the present invention. Non-limiting acids include $H_2SO_4$, $HClO_4$, $H_3PO_4$, $CH_3SO_3H$, $CF_3SO_3H$, $CF_3COOH$, $CH_3COOH/H_2SO_4$, and any combination thereof. Each possibility represents a separate embodiment of the present invention. A currently preferred acid is $H_2SO_4$.

In some embodiments, step (b) of the process, i.e., electrochemical generation of $H_2$, is carried out by electrochemical oxidation of the polyoxometalate using electrodes known in the art such as one selected from Au, Ag, Ni, Co, Pt, Pd, Cu, Al, Au/Ag, Au/Cu, Au/Ag/Cu, Au/Pt, Au/Pd, Au/Ag/Cu/Pd, Pt—Rh, Ni—Co, and Pt—Ni—Fe electrode. A currently used electrode is a platinum gauze electrode.

Water Gas Shift Reaction

Water gas shift reaction (27-29) has been known from 18th century without any industrialization until the beginning of 20th century when people realized its utility for the production of hydrogen to fulfill the requirement of Haber-Bosch process. The exothermic and reversible reaction between the water vapor and carbon monoxide to produce hydrogen and carbon dioxide ($CO+H_2O\rightarrow CO_2+H_2$, $\Delta H=-41.1$ kJ/mol) is known as water gas shift (WGS) reaction.

Industrially, the WGS reaction is carried out in two different temperatures: (a) high temperature WGS (300-450° C.) using Fe-based catalysts (e.g., $Fe_2O_3/Cr_2O_3$) and (b) s:low temperature WGS (200-270° C.) using Cu-based catalysts (e.g., $Cu/ZnO/Al_2O_3$). The necessity of the development of WGS are (i) to produce hydrogen for the fulfillment of Haber-Bosch process for ammonia synthesis (ii) for the removal of carbon monoxide, which act as poison in system like PEM fuel cell. Carbon monoxide together with hydrogen is a useful precursor for Fischer-Tropsch synthesis of hydrocarbons and alcohols.

As demonstrated herein, in the methods of the present invention, CO is partially oxidized to $CO_2$ during the transformation of biomass. In the past such a transformation has been carried out using a polyoxometalate together with a gold catalyst.(30) The present invention is based on the discovery that polyoxometalate $H_5PV_2Mo_{10}O_{40}$ alone in a mineral acid could be used to carry out a water gas shift reaction at very low temperatures. Such a water gas transformation is an improved alternative to the higher temperature water gas shift reaction presently practiced because (1) it is thermodynamically more efficient at low temperature ($\Delta G_{r,g,25°\,C.}=-5.8$ kcal/mol) and (ii) the separate catalytic $CO_2$ and electrochemical $H_2$ forming steps obviate the necessity of separating $CO_2$ from $H_2$. For example, in a glass pressure tube 2 bar of CO was reacted with 1.4 mmol $H_5PV_2Mo_{10}O_{40}\cdot36H_2O$ dissolved in 8 mL 80% aqueous $H_2SO_4$. After 5 h at 100° C. complete conversion was attained and $H_2$ was released electrochemically as described above.

Accordingly, another embodiment of the present invention relates to a method for preparing hydrogen ($H_2$) from biomass or a component thereof, or from a carbohydrate, the method comprising the steps of (a) contacting the biomass, biomass component or carbohydrate with a polyoxometalate catalyst or a solvate thereof in the presence of a concentrated acid under conditions sufficient to produce carbon dioxide ($CO_2$); and (b) electrochemically producing hydrogen ($H_2$); wherein steps (a) and (b) are performed simultaneously or sequentially. Any of the reaction conditions described above, including the type of biomass, acid, etc. may be used for this process. Each possibility represents a separate embodiment of the present invention.

For the production of $CO_2$ by including the water gas shift reaction, the ratio of polyoxometalate per carbon atom in the carbohydrate, biomass or biomass component is generally higher than in the corresponding process for preparing CO. For example, the ratio of polyoxometalate to carbohydrate, biomass or biomass component is preferably greater than 1 equivalent, for example about 2 equivalents or greater of polyoxometalate per carbon atom in the carbohydrate, biomass or biomass component. In some embodiments, the ratio of polyoxometalate to carbohydrate, biomass or biomass component is from greater than 1 to about 2 equivalents of polyoxometalate per carbon atom in the carbohydrate, biomass or biomass component. The aforementioned conditions are preferred for the water gas shift reaction in accordance with some embodiments of the present invention.

A representation of the water gas shift reaction is presented in FIG. 2B, wherein the oxidation of CO is shown along with the electrochemical oxidation of the electrons and protons initially stored on the polyoxometalate.

Polyoxometalate Catalysts

A variety of polyoxometalate catalysts can be used in the methods of the present invention. In some embodiments, the catalysts are soluble polyoxoanion salts represented by the general formula $[X_xM_mO_y]^{q-}$ or a solvate thereof, wherein X is a metal or non-metal heteroatom, or a proton; M are addenda atoms selected from the group consisting of tungsten (W), molybdenum (Mo), niobium (Nb), vanadium (V), tantalum (Ta), bismuth (Bi), antimony (Sb), tin (Sn) and any combination thereof; O is oxygen; x is an integer between 0 and 6; m is an integer between 4 and 200; y is an integer between 5 and 1000; and q is an integer between 0 and 30.

One non-limiting class of polyoxometalate catalysts are Keggin compounds represented by the general formula $Q_q[XM_{12}O_{40}]$, or a solvate thereof, wherein X is selected from the group consisting of (i) B, Al, Ga, In, Si, Ge, Sn, P, As, Sb, S, Se, Te; (ii) a proton; and (iii) a transition metal selected from Sc, Ti, V, Cr, Mn, Fe, Co, Ni, Cu and Zn; M is selected from the group consisting of tungsten (W), molybdenum (Mo) and combinations thereof, wherein the tungsten and/or molybdenum are in a high valence state such as +4, +5 or +6; Q is a counter cation selected from a proton, an alkali metal, an alkaline earth metal, a transition metal including lanthanides or actinides, a main group metal, and an organic cation such as a quaternary ammonium or phosphonium cation; and q is an integer between 0 and 30. The Keggin structure has an approximate tetrahedral symmetry based on a central $XO_4$ tetrahedron surrounded by twelve $MO_6$ octahedra arranged in four groups of three edge shared octahedra, $M_3O_{13}$. Without wishing to be bound by any particular mechanism or theory, one may distinguish between four kinds of oxygen atoms, 4 internal oxygens connecting the heteroatom to the addenda, 12 edge sharing oxygens, 12 corner sharing oxygens connecting $M_3O_{13}$ units, and 12 terminal oxygens.

In some embodiments, the polyoxometalate catalyst is represented by the general formula $Q_q[XM_{12-n}M'_nO_{40}]$, or a solvate thereof, wherein Q, X, M and n are as defined above; M' selected from the group consisting of niobium (Nb), tantalum (Ta), antimony (Sb), bismuth (Bi), tin (Sn) and vanadium (V); and n is 0, 1, 2, 3, 4, 5 or 6. In other embodiments, the polyoxometalates are vanadium substituted molybdates represented by the formula $Q_q[XMo_{12-n}V_nO_{40}]$. Each possibility represents a separate embodiment of the present invention. In one currently preferred embodiment, the polyoxometalate catalyst is $H_5PV_2Mo_{10}O_{40}$.

Polyoxometalate catalysts are often found in solvated forms, for example hydrates. Thus, the present invention encompasses the use of polyoxometalate solvates, such as but not limited to polyoxometalate hydrates. Other solvate molecules of polyoxometalate catalysts include, but are not limited to diethylether, acetonitrile, dimethylsulfoxide, tetrahydrofuran, methanol, ethanol solvates and so forth. The amount of solvate molecules can vary from less than one to a few hundred. Each possibility represents a separate embodiment of the present invention.

A currently preferred solvated form is a hydrate. Thus, the polyoxometalate catalysts of the present invention may be in the form of a hemihydrate, hydrate, sesquihydrate, dihydrate, trihydrate, or multi-hydrate wherein the number of water molecules can be up to a few hundred. In some embodiments, the polyoxometalate catalyst is a hydrated form of $H_5PV_2Mo_{10}O_{40}$, such as $H_5PV_2Mo_{10}O_{40} \times nH_2O$ wherein n is 0 to 36. Generally, the number of water molecules can range from about ½ and 500 molecules of water. Each possibility represents a separate embodiment of the present invention. In one particular embodiment, the polyoxometalate is $H_5PV_2Mo_{10}O_{40} \times 36H_2O$.

The polyoxometalate catalysts used in the methods of the present invention can exist in many isomeric forms, each of which is encompassed by the present invention.

It should be apparent to a person of skill in the art that any ratio of catalyst to carbohydrate that appears appropriate to a person of skill in the art can be used in the context of the present invention.

Biomass

The term "biomass" as used herein refers to a biological material derived from living, or recently living organisms. The biomass is preferably terrestrial biomass. Biomass remains the largest biomass energy source to date; examples include forest residues (such as dead trees, branches and tree stumps), yard clippings, wood chips and even municipal solid or agricultural waste. Biomass can be produced from numerous types of plants, including but not limited to miscanthus, switchgrass, hemp, corn, poplar, willow, sorghum, sugarcane, bamboo, sugar cane, bagasse, cotton, and a variety of tree species, such as pine, beech wood, walnut, eucalyptus, and palm oil. Biomass may also be produced from straw, which is an agricultural by-product, the dry stalks of cereal plants, after the grain and chaff have been removed. Straw makes up about half of the yield of cereal crops such as barley, oats, rice, rye and wheat. Biomass may also be produced from cardboard. Any biomass source described above, as well as other biomass sources, can be used to produce CO and $H_2$ according to the principles of the present invention, with each possibility representing a separate embodiment of the present invention.

Typically, terrestrial biomass contains 35-50% cellulose, 20-35% hemicellulose, and 10-25% lignin.

The term "cellulose" as used herein refers to a polysaccharide consisting of a linear chain of several hundred to over ten thousand β(1-4) linked D-glucose units, $(C_6H_{12}O_6)_n$. is an important structural component of the primary cell wall of green plants, many forms of algae and oomycetes. Included in this term are all known forms of cellulose such as powder cellulose and microcrystalline cellulose.

The term "hemicellulose" as used herein refers to any of several heteropolymers (matrix polysaccharides), present along with cellulose in almost all plant cell walls. Hemicelluloses include xylan, glucuronoxylan, arabinoxylan, glucomannan, and xyloglucan. While cellulose contains only anhydrous glucose, monomers in hemicellulose can include xylose, mannose, galactose, rhamnose, and arabinose. Hemicelluloses contain most of the D-pentose sugars, and occasionally small amounts of L-sugars.

The term "lignin" as used herein refers to a highly cross-linked hydroxylated and methoxylated phenylpropane polymer formed by oxidative coupling of para-hydroxycinnamyl alcohols biochemically derived from the amino acid phenylalanine. Lignin is an integral part of the secondary cell walls of plants.

Carbohydrates

The term "carbohydrate" as used herein refers to organic compound comprising carbon, hydrogen, and oxygen, typically with the empirical formula $C_m(H_2O)_n$ (wherein m is the same or different from n). The term carbohydrate is synonymous with the term "saccharide", which includes monosaccharides, disaccharides, trisaccharides, oligosaccharides, and polysaccharides. The carbohydrate may be derived from plant biomass or from any other natural or synthetic source.

"Monosaccharide" refers to polyhydroxyaldehyde (aldose) or polyhydroxyketone (ketose) and derivatives and analogs thereof. The monosaccharide can be in D- or L-configuration. Monosaccharides may be in the form of D- or L-cyclic sugars in the pyranose (6-membered ring) or furanose (5-membered ring) forms. Furthermore, monosaccharides include 5-carbon sugar (pentoses) or 6-carbon sugars (hexoses). Examples of monosaccharides include, but are not limited to, allose, altrose, arabinose, cladinose, erythrose, erythrulose, fructose, fucose, fuculose, galactose, glucose, glucose-6-phosphate, gulose glyceraldehyde, L-glycero-D-mannos-heptose, glycerone, gulose, idose, lyxose, mannose, mannose-6-phosphate, psicose, quinovose, rhamnose, ribose, ribulose, sedoheptulose, sorbose, tagatose, talose, threose, xylose and xylulose. The monosaccharide may further be a deoxy sugar (alcoholic hydroxy group replaced by hydrogen), a C-substituted monosaccharide (hydrogen at a non-terminal carbon atom replaced with carbon), an unsaturated monosaccharide, an alditol or sugar alcohol (carbonyl group replaced with CHOH group) (e.g., sorbitol, glycol, glycerol, erythritol, threitol, arabitol, xylitol, ribitol, mannitol, galacitol, fucitol, iditol, inositol, volemitol, osomalt, maltitol, lactitol, maltotriitol, maltotetraitol, polyglycitol, rhamnitol and the like), aldonic acid (aldehydic group replaced by carboxy group) (e.g., gluconic acid), a ketoaldonic acid, a uronic acid, an aldaric acid (e.g., tartaric acid), and so forth.

Monosaccharides can be linked together to form disaccharides, trisaccharides, oligosaccharides or polysaccharides. "Polysaccharide" refers to polymers formed from about 500 to over 100,000 saccharide units linked to each other by hemiacetal or glycosidic bonds. The terms "disaccharide", "trisaccharide" and "polysaccharide" include, but are not limited to, abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructooligosachharide, galtooligosaccharide, gentianose, gentiobiose, glucan, glucogen, glycogen, hamamelose, heparin, inulin, isolevoglucosenone, isomaltose, isomaltotriose, isopanose, kojibiose, lactose, laminarabiose, levoglucosan, levoglucosenone, β-maltose, maltriose, mannan-oligosaccharide, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α-trehalose, turanose, tyvelose, xylobiose, xylan, umbelliferose, starch and starch derivatives, and the like.

In one embodiment, the carbohydrate is a polysaccharide derived from terrestrial biomass, i.e., cellulose, hemicellulose or a combination thereof as described above.

As used herein and in the appended claims the singular forms "a", "an," and "the" include plural references unless the content clearly dictates otherwise.

All references cited herein are hereby incorporated by references in their entirety as if fully set forth herein.

The principles of the present invention are demonstrated by means of the following non-limitative examples.

EXPERIMENTAL DETAILS SECTION

EXAMPLE 1

Conversion of Glucose Under Aerobic Conditions

Based on mechanistic analysis of on electron transfer-oxygen transfer reactions catalyzed by $H_5PV^V_2Mo_{10}O_{40}$ in general (22,23) and alcohols and vicinal alcohols in particular (15), it is contemplated that oxidation of D-glucose could yield 5 equivalents of HCOOH, 1 equivalent of HCHO and 6 equivalents of reduced polyoxometalate, $H_7PV^{IV}_2Mo_{10}O_{40}$ according to a series of reactions presented in Scheme 2.

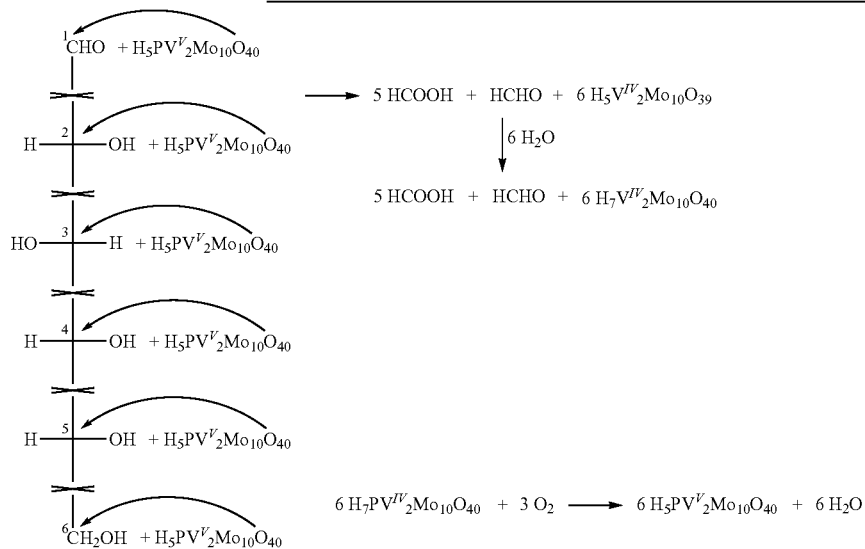

Scheme 2. The projected oxidative cleavage of D-glucose, presented as a Fisher projection for simplicity, by six eqivalents of $H_5PV^V_2Mo_{10}O_{40}$.

Without wishing to be bound by any particular theory or mechanism of action, it is surmised to ideally proceed via an oxygen atom insertion from the polyoxometalate accompanied by carbon-carbon bond cleavage to yield formic acid (HCOOH) from the C-1 to C-5 carbon atoms and formaldehyde (HCHO) from the C-6 carbon atom. The deoxygenated and reduced polyoxometalate, $H_5PV^{IV}_2Mo_{10}O_{39}$ reacts with $H_2O$ to yield $H_7PV^{IV}_2Mo_{10}O_{40}$. If the reaction is carried out in the presence of $O_2$, its reaction with $H_7PV^{IV}_2Mo_{10}O_{40}$ will yield $H_5PV^{IV}_2Mo_{10}O_{40}$ and $H_2O$. The 2 electrons and 2 protons, or oxidized H₂, per polyoxometalate unit, $H_7PV^{IV}_2Mo_{10}O_{40}$, will be lost or wasted.

The oxidation of D-glucose as suggested in Scheme 2 was tested using methanol/water as a solvent, which allowed reaction under relatively mild conditions compared to the literature reports,(16,17) especially not requiring high O₂ pressures. Thus, 100 mg (0.56 mmol) D-glucose and 80 mg (0.038 mmol) $H_5PV_2Mo_{10}O_{40}\cdot 36H_2O$ were dissolved in a 3 mL (1:1) mixture of methanol and water and the solution was heated to 110° C. for 18 h under 2 bar O₂. Under these conditions, essentially quantitative conversions of D-glucose were obtained according to Scheme 3, where the presence of methanol in the acidic reaction medium leads to further partial ester, hemiacetal and acetal formation. It should be noted that methanol is oxidized only in trace amounts under these conditions.

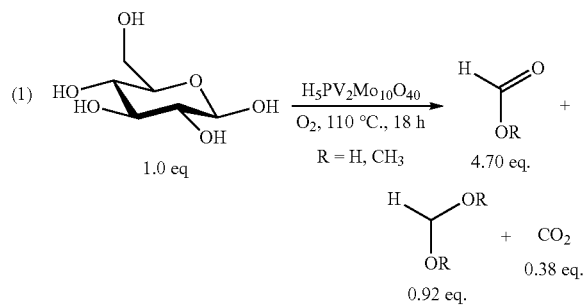

Scheme 3

As seen, the results demonstrate a good correlation with the expected theoretical results presented in Scheme 2.

EXAMPLE 2

Conversion of Carbohydrates Under Aerobic Conditions

The conversion of other carbohydrates was carried out by 100 mg reacting and 80 mg $H_5PV_2Mo_{10}O_{40}$ in 3 mL (1:1) methanol/water under 2 bar O₂ at 110° C. for 18 h. The amount of products is given as per carbon atoms of substrate that reacted are given in Table 1.

TABLE 1

Aerobic oxidation of a variety of saccharides and polysaccharides.

| Substrate | Conversion, mol % | HCOOR R = H, CH₃ | H₂C(OR)₂ R = H, CH₃ | CO₂ | CO |
|---|---|---|---|---|---|
| D-glucose | >99 | 4.70 | 0.92 | 0.38 | nd |
| gluconic acid | >99 | 4.00 | 0.59 | 1.09 | 0.22 |
| D-galactose | >99 | 4.78 | 0.86 | 0.36 | nd |
| D-mannose | >99 | 4.66 | 0.91 | 0.43 | nd |
| sorbitol[a] | >99 | 3.89 | 1.55 | 0.39 | 0.17 |
| fructose | >99 | 3.94 | 1.63 | 0.43 | nd |
| xylan | >99 | 3.84 | 0.78 | 0.38 | nd |
| cellulose[b] | ~40 | 1.57 | 0.56 | 0.34 | nd | nd—not detected.
[a]30 h.
[b]120° C., 30 h.

EXAMPLE 3

Conversion of Carbohydrates to CO in Concentrated $H_2SO_4$

According to Scheme 4, cellulose or hemicellulose can be transformed to CO and a reduced polyoxometalate. The cellulose used was microcrystalline powder from natural wood pulp and the hemicellulose was xylan from beech wood. Both were used without any pre-treatment. The reactions were carried out by mixing 100 mg polysaccharide and 7.80 g $H_5PV_2Mo_{10}O_{40}$ in 8 mL concentrated $H_2SO_4$ at 70° C. for 5 h under an N2 atmosphere. As the polyoxometalate is solvated by 36 water molecules, the concentration of $H_2SO_4$ during the reaction is ~80%. There was complete conversion for both cellulose and hemicellulose and analysis of the gas phase by gas chromatography with a thermal conductivity detector (GC-TCD) showed the formation of only CO and CO₂ in a ratio that was on the average 65±3:35±3 over five experiments. In addition, quantitative analysis using the GC-TCD with N2 as the internal standard showed quantitative formation, that is, 97±4% of CO and CO₂.

The degree of reduction of $H_5PV_2Mo_{10}O_{40}$ was determined by titration with $KMnO_4$. Averaging over five cellulose oxidation experiments, 2.7±0.2 equivalent electrons per equivalent carbon atom were measured. Since vanadium is reduced prior to molybdenum, (22,23) by reaction stoichiometry $H_7PV^{IV}_2Mo^{VI}_{10}O_{40}$ and $H_8PV^{IV}_2Mo^{VI}_9O_{40}$ are apparently present in the reaction mixture in a ~3:7 ratio.

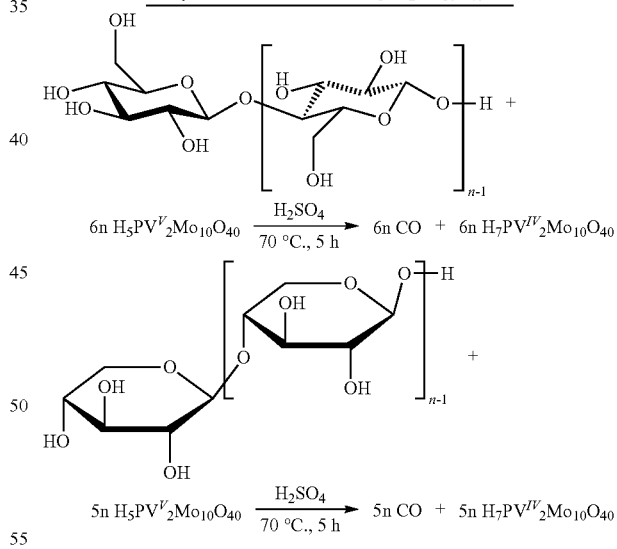

Scheme 4. Anaerobic oxidation of cellulose and xylan hemicellulose with $H_5PV_2Mo_{10}O_{40}$.

EXAMPLE 4

Conversion of CO

The reason for the formation of CO₂ under the conditions presented in Example 3 was not immediately clear. A reaction according to Example 3 demonstrates that after only 30 min the CO:CO₂ ratio was 5:1, and therefore it was contemplated that CO was being oxidized by $H_5PV_2Mo_{10}O_{40}$. Indeed addition of ~2 mmol CO to a 0.42

M solution of $H_5PV_2Mo_{10}O_{40}$ in $H_2SO_4$ showed the formation of $CO_2$ with ~40% conversion after 5 h at 70° C. (Scheme 5):

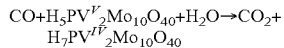
  Scheme 5. Oxidation of CO

EXAMPLE 5

Conversion of Cellulose to CO in Various Solvents

The conversion of cellulose in various acid solvents was carried out by mixing 100 mg cellulose and 7.80 g $H_5PV_2Mo_{10}O_{40}$ were mixed in 8 mL solvent under N2 as presented in Table 2.

TABLE 2

Anaerobic oxidation of cellulose with different acid solvents.

| Solvent | Time, h | Temperature, ° C. | Conversion, mol % | Ratio CO/$CO_2$ |
|---|---|---|---|---|
| 98% $H_2SO_4$ | 5 | 70 | 100 | 65/35 |
| 90% $H_2SO_4$ | 5 | 70 | 100 | 65/35 |
| 80% $H_2SO_4$ | 7 | 80 | 100 | 67/33 |
| 50% $H_2SO_4$ | 18 | 140 | 84 | 45/29 |
| 70% $HClO_4$ | 8 | 110 | 75 | 15/60 |
| 85% $H_3PO_4$ | 8 | 110 | 84 | 48/28 |
| $CH_3SO_3H$ | 5 | 70 | 42 | 30/12 |
| $CF_3SO_3H$ | 5 | 70 | 67 | 45/22 |
| $CF_3COOH$ | 5 | 70 | 56 | 6/50 |
| $CH_3COOH/H_2SO_4$ 4:1 | 8 | 120 | 95 | 50/45 |

Reaction conditions: 100 mg polysaccharide, 7.80 g (3.3 mmol) $H_5PV_2Mo_{10}O_{40} \cdot 36H_2O$, 8 mL solvent, 70° C., 5 h, N2. Since the polyoxometalate is solvated with $H_2O$ there is in addition another 1.9 mL $H_2O$ in the reaction mixture.

EXAMPLE 6

Release of $H_2$

Figure 1B:
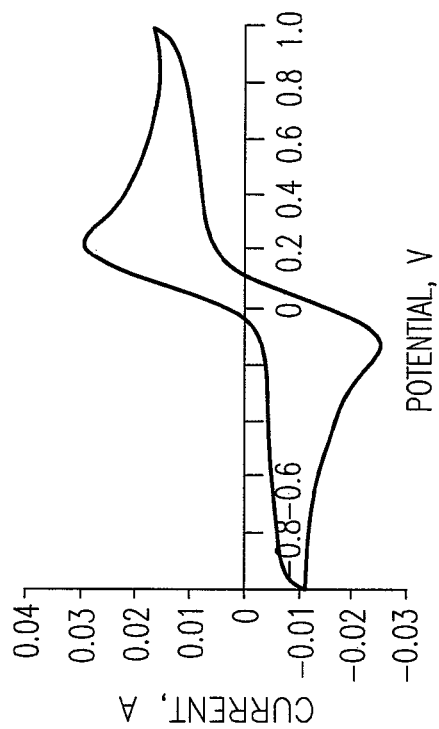
FIG. 1B—after oxidation at 0.6 V and 25-30% oxidation of the polyoxometalate leaving 2.0 electrons/$H_5PV_2Mo_{10}O_{40}$.

The cyclic voltammetry measurements of this reaction solution, 0.42 M $H_5PV_2Mo_{10}O_{40}$ in $H_2SO_4$ reduced by 2.7 electrons, FIG. 1A, showed a redox potential of 0.4 V versus NHE. Oxidation of 25-30% of the polyxometalate at 0.6 V resulted in a change in the color of the solution to a dark green and a shift of the redox potential to 0.05 V versus NHE, FIG. 1B. From this it would appear that first $H_8PV^{IV}_2Mo^V Mo^{VI}_9O_{40}$ is oxidized to $H_7PV^{IV}_2Mo^{VI}_{10}O_{40}$, which is then oxidized to $H_5PV^V_2Mo_{10}O_{40}$. Therefore, in order to form $H_2$ quantitatively the solution was oxidized using a Pt gauze electrode. Oxidation was at 0.6 V for 25-30% of the total number of coulombs needed and then the oxidation of the polyoxometalate was completed at 0.2 V. The total coulomb count gave the same average amount of electrons as the $KMnO_4$ titration. Hydrogen was collected and its quantitative formation verified by GC-TCD.

Materials and Methods for Examples 1-6

Materials. Microcrystalline cellulose, hemicellulose, and the other sugars were purchased from Sigma-Aldrich. Microcrystalline cellulose was used without pre-treatment. $H_5PV_2Mo_{10}O_{40} \cdot 36H_2O$ was prepared by a known procedure.(25)

Methods.

(1) Aerobic reactions in water/methanol: 100 mg saccharide or polysaccharide, 80 mg $H_5PV_2Mo_{10}O_{40} \cdot 36H_2O$ (0.038 mmol) were dissolved in 3 mL of a (1:1) mixture of $CD_3OD$ and $D_2O$ in a 50 mL glass pressure tube. Reactions were carried at 2 bar $O_2$, 110° C. for 18 h. The amount of products formed, formic acid, methyl formate, dimethoxymethane, methoxymethanol, and methanediol were calculated using 300 MHz $^1H$ NMR and ethanol as an external standard. Since the peak for $H_2O$ (always present to some degree) partially overlapped with those of the formaldehyde derivatives, 2 drops of 35% HCl were added to shift the peak of water downfield. $CO_2$ and CO were determined by GC-TCD using a GowMac instrument with a 20'×⅛" stainless steel column packed with molecular Sieve 5 Å in series with a 4'×⅛" stainless steel column packed with HayeSep T. The carrier gas was Ar, column T=120° C. Retention times for $CO_2$ —4.5 min; CO—30.2 min.

(2) Anaerobic oxidation in concentrated (98%) sulfuric acid and hydrogen formation: 100 mg cellulose or hemicellulose and 7.80 g (3.3 mmol) $H_5PV_2Mo_{10}O_{40}$ were mixed in 8 mL $H_2SO_4$. At room temperature this is a slurry but upon heating a clear solution is obtained. The reaction was carried out at 70° C. for 5 h under N2. CO and $CO_2$ were analyzed as described above. $H_2$ was formed electrochemically using a platinum gauze, 25-30% oxidation at 0.7 V and the remainder at 0.2 V. $H_2$ was quantified by GC-TCD using a GowMac instrument with a 20'×⅛" stainless steel column packed with molecular Sieve 5 Å in series with a 4'×⅛" stainless steel column packed with HayeSep T. The carrier gas was Ar, column T=120° C. Retention time—10 min.

(3) Anaerobic oxidation of cellulose in various acid solvents: 100 mg cellulose and 7.80 g (3.3 mmol) $H_5PV_2Mo_{10}O_{40}$ were mixed in 8 mL solvent. Reactions were performed at 70° C. for 5 h.

(4) Cyclic voltammetry experiments: These experiments were performed using a potentiostat (CHI660A) connected to a personal computer. The measurements were performed in a three-electrode cell configuration consisting of (i) Platinum gauze (working electrode), (ii) a Pt wire (counter electrode), and (iii) Pt (a reference electrode). The experiments were performed at room temperature. The scan rate was 200 mV/sec.

(5) Titration with $KMnO_4$: The concentration of fresh $KMnO_4$ solutions where determined by volumetric titration with a standard oxalic acid solutions. The reduced polyoxometalate solutions were titrated volumetrically using the disappearance of the peak of the reduced polyoxometalate at 750 nm as indicator.

Conclusions of Examples 1-6

In summary, based on the foregoing experiments, the following conclusion may be made:

(1) The present invention provides the first reported use of concentrated sulphuric acid, an inexpensive industrial commodity, in a polyoxometalate-catalysed reaction that now allows the complete transformation of both cellulose and hemicellulose as well as other biomass and biomass components at mild reaction temperatures. The initially formed formic acid is formed in a high yield and then quantitatively dehydrated to CO. The electrochemical release of $H_2$ for the most part at a relatively low over-potential of 0.2V allows the overall formation of synthesis gas, 1 equivalent of CO and $H_2$ per carbon atom.

(2) The use of $H_2SO_4$ has the added advantage that it significantly increases the rate of the electron transfer-oxygen transfer oxidation and is a convenient medium for the release of $H_2$ at low potentials.

(3) Fast removal of the CO formed by purging the reaction mixture can prevent its further oxidation to $CO_2$. However, if $H_2$ were the target, the complete conversion of CO by a water-gas shift reaction using this catalytic system can be used. In this way, 2 equivalents of $H_2$ can be formed per carbon atom in the polysaccharide (see Example 7).

(4) The separate electrochemical release of $H_2$ can allow separate formation of $H_2$ and CO. These may be combined into Syngas in accordance with some embodiments of the present invention. Alternatively, if separate $H_2$ formation is desired, it can be generated independently of CO.

(5) Importantly, after the formation of only gaseous products, the reaction solution, that is, $H_5PV_2Mo_{10}O_{40}$ in $H_2SO_4$, can be recycled and reused without any additional treatment. Ten reaction cycles using cellulose as substrate showed no change in reactivity.

EXAMPLE 7

Water Gas Shift Reaction

A water gas shift (WGS) reaction was carried out at ambient conditions as shown in Table 3.

TABLE 3

WGS reactions carried out over different polyoxometalate

| Polyoxometalate | Temperature (° C.) | Time (h) | % Conversion[a] |
|---|---|---|---|
| $H_5PV_2Mo_{10}O_{40}$ | 70 | 6 | 40 |
| $H_5PV_2Mo_{10}O_{40}$ | 70 | 12 | 60 |
| $H_5PV_2Mo_{10}O_{40}$ | 80 | 12 | 80 |
| $H_5PV_2Mo_{10}O_{40}$ | 80 | 24 | 100 |
| $H_5PV_2Mo_{10}O_{40}$ | 100 | 8 | 90 |
| $H_5PV_2Mo_{10}O_{40}$ | 100 | 10 | 100 |
| $H_5PV_2Mo_{10}O_{40}$ | 120 | 5 | 100 |
| $H_4PV_1Mo_{11}O_{40}$ | 70 | 8 | 30 |
| $H_4PV_1Mo_{11}O_{40}$ | 80 | 10 | 50 |
| $H_4PV_1Mo_{11}O_{40}$ | 100 | 12 | 80 |
| $H_4PV_1Mo_{11}O_{40}$ | 120 | 12 | 100 |
| $H_6PV_3Mo_9O_{40}$ | 70 | 6 | 50 |
| $H_6PV_3Mo_9O_{40}$ | 80 | 12 | 90 |
| $H_6PV_3Mo_9O_{40}$ | 100 | 5 | 100 |

Reaction Conditions: All the reactions were carried out in Fisher-Portar pressure tube taking 2 atm CO, 3 g of polyoxometalate (1.38 mmol), 8 mL of 80% sulfuric acid. (a) Conversions were based on the polyoxometalate used. $H_2$ was formed electrochemically using a platinum gauze, 25-30% oxidation at 0.7 V and the remainder at 0.2 V. $H_2$ was quantified by GC-TCD using a GowMac instrument with a 20'×⅛" stainless steel column packed with molecular Sieve 5 Å in series with a 4'×⅛" stainless steel column packed with HayeSep T. The carrier gas was Ar, column T=120° C. Retention time—10 min.

EXAMPLES 8-11

Conversion of Biomass (Wheat Straw)

Milled wheat straw was reacted with $H_5PV_2Mo_{10}O_{40}$ in 5 mL 80% $H_2SO_4$ under 1 bar N2 in a 15 mL glass tube according to the amounts and conditions shown in Table 4. The results are also given in Table 3. $H_2$ was recovered by electrolysis at 0.5 V using platinum working, reference and counter electrodes. Approximately 1 equivalent of $H_2$ was formed per equivalent CO and 2 equivalents of $H_2$ were formed per equivalent $CO_2$.

TABLE 4

| Example | Wheat Straw | $H_5PV_2Mo_{10}O_{40}$ | Temp, ° C. | Time, h | Yield, mol % | % CO | % $CO_2$ |
|---|---|---|---|---|---|---|---|
| 9 | 35 mg | 3 g | 70 | 2 | 80 | 50 | 30 |
| 10 | 10 mg | 1 g | 70 | 3 | 82 | 48 | 34 |
| 11 | 35 mg | 3 g | 70 | 6 | 83 | 44 | 39 |
| 12 | 35 mg | 3 g | 60 | 2 | 76 | 55 | 21 |

The yield was calculated as total CO and $CO_2$ formed in mols relative to 1 bar N2 translated to mol according to PV=nRT. $CO_2$ and CO were determined by GC-TCD using a GowMac instrument with a 20'×⅛" stainless steel column packed with molecular Sieve 5 Å in series with a 4'×⅛" stainless steel column packed with HayeSep T. The carrier gas was Ar, column T=120° C. Retention times for $CO_2$—4.5 min; CO—30.2 min.

EXAMPLES 12-15

Conversion of Various Biomass

The milled biomass samples (20 mg) were reacted with 2 g $H_5PV_2Mo_{10}O_{40}$ in 5 mL 80% $H_2SO_4$ at 60° C. for 4 h under 1 bar N2 in a 15 mL glass tube. The results are given in Table 5. $H_2$ was recovered by electrolysis at 0.5 V using platinum working, reference and counter electrodes. Approximately 1 equivalent of $H_2$ was formed per equivalent CO and 2 equivalents of $H_2$ were formed per equivalent $CO_2$.

TABLE 5

| Example | Biomass | Yield, mol % | % CO | % $CO_2$ |
|---|---|---|---|---|
| 13 | Pine tree | 78 | 48 | 30 |
| 14 | Beachwood | 75 | 46 | 29 |
| 15 | African walnut | 75 | 48 | 27 |
| 16 | Cardboard | 84 | 56 | 28 |

The yield was calculated as total CO and $CO_2$ formed in mols relative to 1 bar N2 translated to mol according to PV=nRT. $CO_2$ and CO were determined by GC-TCD using a GowMac instrument with a 20'×⅛" stainless steel column packed with molecular Sieve 5 Å in series with a 4'×⅛" stainless steel column packed with HayeSep T. The carrier gas was Ar, column T=120° C. Retention times for $CO_2$—4.5 min; CO—30.2 min.

EXAMPLES 16-19

Conversion of Lignin

Lignin (alkaline from TCI) was reacted with $H_5PV_2Mo_{10}O_{40}$ in 5 mL 80% $H_2SO_4$ under 1 bar N2 in a 15 mL glass tube according to the amounts and conditions shown in Table 5. The results are also given in Table 6. $H_2$ was recovered by electrolysis at 0.5 V using platinum working, reference and counter electrodes. Approximately 1 equivalent of $H_2$ was formed per equivalent CO and 2 equivalents of $H_2$ were formed per equivalent $CO_2$.

TABLE 6

| Example | Lignin | $H_5PV_2Mo_{10}O_{40}$ | Temperature, °C | Time, h | Yield CO | Yield $CO_2$ |
|---|---|---|---|---|---|---|
| 17 | 20 mg | 1 g | 80 | 7 | 15 | 45 |
| 18 | 50 mg | 3 g | 70 | 5 | 13 | 52 |
| 19 | 10 mg | 1 g | 100 | 5 | 4 | 61 |
| 20 | 10 mg | 1 g | 80 | 5 | 18 | 42 |

The yields of CO and $CO_2$ were calculated as formed in mols relative to 1 bar N2 translated to mol according to PV=nRT. $CO_2$ and CO were determined by GC-TCD using a GowMac instrument with a 20'×⅛" stainless steel column packed with molecular Sieve 5 Å in series with a 4'×⅛" stainless steel column packed with HayeSep T. The carrier gas was Ar, column T=120° C. Retention times for $CO_2$ —4.5 min; CO—30.2 min.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES

1. C.-H. Zhou, X. Xia, C.-X. Lin, D.-S. Tong, J. Beltramini, Catalytic conversion of lignocellulosic biomass to fine chemicals and fuels. *Chem. Soc. Rev.* 40, 5588-5617 (2011).
2. J. A. Melero, J. Iglesias, A. Garcia, Biomass as renewable feedstock in standard refinery units. Feasibility, opportunities and challenges. *Energy Environ. Sci.* 5, 7393-7420 (2012).
3. L. T. Fan, M. M. Gharpuray, Y. H. Lee, *Cellulose Hydrolysis* (Springer-Verlag, Berlin, 1987).
4. L. Zhu, J. P. O'Dwyer, V. S. Chang, C. B. Brabda, M. Y. Holtzapple, Structural features affecting biomass enzymatic digestibility. *Bioresource Tech.* 99, 3817-3828 (2008).
5. J. N. Chheda, G. W. Huber, J. A. Dumesic, Liquid-phase catalytic processing of biomass-derived oxygenated hydrocarbons to fuels and chemicals. *Angew. Chem. Int. Ed.* 46, 7164-7183 (2007).
6. G. W. Huber, S. Iborra, A. Corma, Synthesis of transportation fuels from biomass: chemistry, catalysts, and engineering. *Chem. Rev.* 106, 4044-4098 (2006).
7. E. L. Kunkes, D. A. Simonetti, R. M. West, J. C. Serrano-Ruiz, C. A. Gärtner, J. A. Dumesic, Catalytic conversion of biomass to monofunctional hydrocarbons and targeted liquid-fuel classes. *Science*, 322, 417-421 (2008).
8. G. W. Huber, J. N. Chheda, C. J. Barrett, J. A. Dumesic, Production of liquid alkanes by aqueous-phase processing of biomass-derived carbohydrates. *Science*, 308, 1446-1449 (2005).
9. A. D. Sutton, F. D. Waldie, R. Wu, M. Schlaf, L. A. 'Pete' Silks III, J. C. Gordon, The hydrodeoxygenation of bio-derived furans into alkanes. *Nature Chem.* 5, 428-432 (2013).
10. G. W. Huber, J. W. Shabaker, J. A. Dumesic, Raney Ni—Sn catalyst for $H_2$ production from biomass-derived hydrocarbons. *Science*, 300, 2075-2077 (2003).
11. T. D. Matson, K. Barta, A. V. Iretskii, Peter C. Ford, One-pot catalytic conversion of cellulose and of woody biomass solids to liquid fuels. *J. Am. Chem. Soc.* 133, 14090-14097 (2011).
12. J. B. Binder, R. T. Raines, Simple chemical transformation of lignocellulosic biomass into furans for fuels and chemicals. *J. Am. Chem. Soc.* 131, 1979-1985 (2009).
13. P. M. Maitlis, A. de Klerk, Greener-Fischer-Tropsch-Processes for Fuels and Feedstocks, Wiley-VCH, Weinheim, 2013
14. A. B. Stiles, Methanol, past, present, and speculation on the future. *AIChE, Journal*, 23, 362-375, (1977).
15. A. M. Khenkin, R. Neumann, Oxidative C—C bond cleavage of primary alcohols and vicinal diols catalyzed by $H_5PV_2M_{10}O_{40}$ by an electron transfer and oxygen transfer mechanism. *J. Am. Chem. Soc.* 130, 14474-14476 (2008).
16. J. Albert, R. Wolfel, A. Bösmann, P. Wasserscheid. Selective oxidation of complex, water-insoluble biomass to formic acid using additives as reaction accelerators, *Energy Environ. Sci.* 5, 7956-7962 (2012).
17. R. Wolfel, N. Taccardi, A. Bösmann, P. Wasserscheid, Selective catalytic conversion of biobased carbohydrates to formic acid using molecular oxygen. *Green Chem.* 11, 2759-2763, (2011).
18. J. Li, D.-J. Ding, L. Deng, Q.-X. Guo, Y. Fu, Catalytic air oxidation of biomass-derived carbohydrates to formic acid. *ChemSusChem*, 5, 1313-1318 (2012).
19. C. Fellay, P. J. Dyson, G. Laurenczy, A viable hydrogen-storage system based on selective formic acid decomposition with a ruthenium catalyst. *Angew. Chem. Int. Ed.* 47, 3966-3968 (2008).
20. Z.-L. Wang, J.-M. Yan, Y. Ping, H.-L. Wang, W.-T. Zheng, Q. Jiang, An efficient CoAuPd/C catalyst for hydrogen generation from formic acid at room temperature. *Angew. Chem. Int. Ed.* 52, 4406-4409 (2103).
21. J. M. Trillo, G. Munuera, J. M. Criado, Catalytic decomposition of formic acid on metal oxides. *Catal. Rev. Sci. Eng.* 7, 51-86 (1972).
22. R. Neumann, Activation of molecular oxygen, polyoxometalates and liquid phase catalytic oxidation. *Inorg. Chem.* 49, 3594-3601 (2010).
23. I. Efremenko, R. Neumann, Computational insight into the initial steps of the Mars-van Krevelen mechanism: Electron transfer and surface defects in the reduction of oolyoxometalates. *J. Am. Chem. Soc.* 134, 20669-20680 (2012).
24. G. Jacobs, B. H. Davis, Low temperature water-gas shift catalysts. Catalysis 20, 122-285 (2007).
25. G. A. Tsigdinos, C. J. Hallada, Molybdovanadophosphoric acids and their salts. I. Investigation of methods of preparation and characterization. *Inorg. Chem.* 7, 437-441 (1968).
26. I. A. Weinstock, R. H. Atalla, R. S. Reiner, M. A. Moen, K. E. Hammel, C. J. Houtman, C. L. Hill, M. K. Harrup *Journal of Molecular Catalysis A: Chemical* 116, 59-84, (1997).
27. David S. Newsome (1980) The Water-Gas Shift Reaction, Catalysis Reviews: Science and Engineering, 21:2, 275-318.
28. Bartholomew, C. H.; Farrauto, R. J. Fundamentals of Industrial Catalytic Processes, 2nd ed.; John Wiley and Sons: 2006.
29. H. P. Dhar, L. G. Christner, and A. K. Kush; *J. Electrochem. Soc.* 1987 134(12), 3021-3026.
30. W. B. Kim, T. Voitl, G. J. Rodriguez-Rivera, J. A. Dumesic, Powering fuel cells with CO via aqueous polyoxometalates and gold catalysts. *Science*, 305, 1280-1283 (2004).

What is claimed is:

1. A method for preparing carbon monoxide (CO) and hydrogen ($H_2$) from biomass or a component thereof, or from a carbohydrate, the method comprising the steps of
   (a) contacting the biomass, biomass component or carbohydrate with a polyoxometalate catalyst or a solvate thereof in the presence of a concentrated acid, under conditions sufficient to produce carbon monoxide (CO) and optionally carbon dioxide ($CO_2$); and
   (b) electrochemically producing hydrogen ($H_2$);
   wherein steps (a) and (b) are performed simultaneously or sequentially.

2. The method according to claim 1, further comprising the step of combining the carbon monoxide (CO) produced in step (a) or a portion thereof, and the hydrogen ($H_2$) produced in step (b) or a portion thereof, so as to form synthesis gas (Syngas).

3. The method according to claim 1, wherein the biomass or component thereof comprises lignin, ligno-cellulose, cellulose, hemicellulose, or any combination thereof.

4. The method according to claim 1, wherein step (a) comprises the use of biomass.

5. The method according to claim 1, further comprising the step of separating the biomass into one or more components thereof prior to step (a), and using one or more of said components in step (a).

6. The method according to claim 5, wherein the biomass is separated into hemi-cellulose and ligno-cellulose, and ligno-cellulose is used in step (a).

7. The method according to claim 5, wherein the biomass is separated into hemi-cellulose and ligno-cellulose, the ligno-cellulose is further separated into lignin and cellulose, and either lignin or cellulose is used in step (a).

8. The method according to claim 1, wherein step (a) comprises the use of a carbohydrate which is optionally derived from biomass.

9. The method according to claim 1 wherein the carbohydrate is selected from the group consisting of monosaccharides, disaccharides, trisaccharides, oligosaccharides, polysaccharides, sugar alcohols, a carbohydrate derived from terrestrial biomass, starch and any combination thereof.

10. The method according to claim 1, wherein steps (a) and (b) are conducted simultaneously as a one-pot reaction.

11. The method according to claim 1, further comprising the step of repeating steps (a) and (b) at least one additional time without recycling or regenerating the polyoxometalate catalyst.

12. The method according to claim 1, further comprising the step of removing CO from the reaction after step (a), wherein said removing step is carried out by purging.

13. The method of claim 1, wherein said method is for preparing carbon monoxide (CO) and optionally carbon dioxide ($CO_2$) wherein the ratio of polyoxometalate to carbohydrate, biomass or biomass component is about 1 equivalent or less of polyoxometalate per carbon atom in the carbohydrate, biomass or biomass component.

14. The method according to claim 1, wherein the polyoxometalate catalyst is a polyoxoanion salt represented by the general formula $[X_xM_mO_y]^{q-}$ or a solvate thereof, wherein
   X is a metal or non-metal heteroatom, or a proton
   M are addenda atoms selected from the group consisting of tungsten (W), molybdenum (Mo), niobium (Nb), vanadium (V), tantalum (Ta), bismuth (Bi), antimony (Sb), tin (Sn) and any combination thereof;
   O is oxygen;
   x is an integer between 0 and 6;
   m is an integer between 4 and 200;
   y is an integer between 5 and 1000; and
   q is an integer between 0 and 30.

15. The method according to claim 14, wherein the polyoxometalate catalyst is represented by the general formula $Q_q[XM_{12}O_{40}]$, or a solvate thereof, wherein
   X is selected from the group consisting of (i) B, Al, Ga, In, Si, Ge, Sn, P, As, Sb, S, Se Te; (ii) a proton; and (iii) a transition metal selected from Sc, Ti, V, Cr, Mn, Fe, Co, Ni, Cu and Zn;
   M is selected from the group consisting of tungsten (W), molybdenum (Mo) and combinations thereof, wherein the tungsten and/or molybdenum are in a high valence state such as +4, +5 or +6;
   Q is a counter cation selected from a proton, an alkali metal, an alkaline earth metal, a transition metal including lanthanides or actinides, a main group metal, and an organic cation such as a quaternary ammonium or phosphonium cation; and
   q is an integer between 0 and 30.

16. The method according to claim 15, wherein the polyoxometalate catalyst is represented by the general formula $Q_q[XM_{12-n}M'_nO_{40}]$, or a solvate thereof, wherein Q, X, M, O and q are as defined in claim 5; M' selected from the group consisting of niobium (Nb), tantalum (Ta), antimony (Sb), bismuth (Bi), tin (Sn) and vanadium (V); and n is 0, 1, 2, 3, 4, 5 or 6.

17. The method according to claim 16, wherein the polyoxometalate catalyst is represented by the general formula the formula $Q_q[XMo_{12-n}V_nO_{40}]$, or a solvate thereof.

18. The method according to claim 17, wherein the polyoxometalate catalyst is $H_5PV_2Mo_{10}O_{40}$ or a solvate thereof.

19. The method according to claim 14, wherein the polyoxometalate is in the form of a hydrate containing between ½ and 500 molecules of water, preferably wherein the polyoxometalate is $H_5PV_2Mo_{10}O_{40}$ $xnH_2O$ wherein n is 0 to 36.

20. The method according to claim 1, wherein the acid is selected from the group consisting of $H_2SO_4$, $HClO_4$, $H_3PO_4$, $CH_3SO_3H$, $CF_3SO_3H$, $CF_3COOH$, $CH_3COOH/H_2SO_4$, and any combination thereof.

21. A method for preparing hydrogen ($H_2$) from biomass or a component thereof, or from a carbohydrate by including a water gas shift reaction; the method comprising the steps of
   (a) contacting the biomass, biomass component or carbohydrate with a polyoxometalate catalyst or a solvate thereof in the presence of a concentrated acid under conditions sufficient to produce carbon dioxide ($CO_2$); and
   (b) electrochemically producing hydrogen ($H_2$);
   wherein steps (a) and (b) are performed simultaneously or sequentially.

22. The method according to claim 21, wherein the ratio of polyoxometalate to carbohydrate, biomass or biomass component is greater than 1 equivalent of polyoxometalate per carbon atom in the carbohydrate, biomass or biomass component.

23. The method according to claim 21, wherein the concentrated acid is present at a concentration of about 50% w/w or greater in water, greater than about 80% w/w in water, or greater than about 90% w/w in water.

24. The method according to claim 21, wherein the acid is selected from the group consisting of $H_2SO_4$, $HClO_4$, H₃PO₄, CH₃SO₃H, CF₃SO₃H, CF₃COOH, CH₃COOH/H₂SO₄, and any combination thereof.

25. The method according to claim 21, wherein the reaction is conducted under aerobic conditions or anaerobic conditions.

26. A method for preparing formic acid from a carbohydrate, the method comprising the step of contacting the carbohydrate with a polyoxometalate catalyst or a solvate thereof and with the optional addition of oxygen, air or any combination thereof in a solvent selected from an alcohol or a mixture of alcohol and water, under conditions sufficient to produce formic acid, wherein the pressure of the oxygen air or any combination thereof is between 1-5 atm.

27. The method according to claim 26, wherein the alcohol is selected from the group consisting of methanol, ethanol, propanol, isopropanol, n-butanol, sec-butanol, isobutanol and t-butanol.

28. The method according to claim 26, wherein the carbohydrate is selected from the group consisting of monosaccharides, disaccharides, trisaccharides, oligosaccharides, polysaccharides, sugar alcohols, terrestrial biomass, starch and any combination thereof.

29. The method according to claim 26, wherein the carbohydrate is derived from terrestrial biomass comprising cellulose, hemicellulose or a combination thereof.

30. The method according to claim 26, wherein the ratio of polyoxometalate to carbohydrate, biomass or biomass component is about 1 equivalent or less of polyoxometalate per carbon atom in the carbohydrate.

31. The method according to claim 26, wherein the reaction is conducted under aerobic conditions or under anaerobic conditions.

32. The method according to claim 26, wherein the polyoxometalate catalyst is a polyoxoanion salt represented by the general formula $[X_xM_mO_y]^{q-}$ or a solvate thereof, wherein
X is a metal or non-metal heteroatom, or a proton
M are addenda atoms selected from the group consisting of tungsten (W), molybdenum (Mo), niobium (Nb), vanadium (V), tantalum (Ta), bismuth (Bi), antimony (Sb), tin (Sn) and any combination thereof;
O is oxygen;
x is an integer between 0 and 6;
m is an integer between 4 and 200;
y is an integer between 5 and 1000; and
q is an integer between 0 and 30.

33. The method according to claim 32, wherein the polyoxorrretalate catalyst is represented by the general formula $Q_q[XM_{12}O_{40}]$, or a solvate thereof, wherein
X is selected from the group consisting of (i) B, Al, Ga, In, Si, Ge, Sn, P, As, Sb, S, Se Te; (ii) a proton; and (iii) a transition metal selected from Sc, Ti, V, Cr, Mn, Fe, Co, Ni, Cu and Zn;
M is selected from the group consisting of tungsten (W), molybdenum (Mo) and combinations thereof, wherein the tungsten and/or molybdenum are in valence state such as +4, +5 or +6;
Q is a counter cation selected from a proton, an alkali metal, a alkaline earth metal, a transition metal including lanthanides or actinides, a main group metal, and an organic cation such as a quaternary ammonium or phosphonium cation; and
q is an integer between 0 and 30.

34. The method according to claim 33, wherein the polyoxometalate catalyst is represented by the general formula $Q_q[XM_{12-n}M'_nO_{40}]$, or a solvate thereof, wherein Q, X, M, O and q are as defined in claim 5; M' selected from the group consisting of niobium (Nb), tantalum (Ta), antimony (Sb), bismuth (Bi), tin (Sn) and vanadium (V); and n is 0, 1, 2, 3, 4, 5 or 6.

35. The method according to claim 34, wherein the polyoxometalate catalyst is represented by the general formula the formula $Q_q[XMo_{12-n}V_nO_{40}]$, or a solvate thereof.

36. The method according to claim 35, wherein the polyoxornetalate catalyst is $H_5PV_2Mo_{10}O_{40}$ or a solvate thereof.

37. The method according to claim 32, wherein the solvate is selected from the group consisting of a hydrate, a diethylether solvate, an acetonitrile solvate, a dimethylsulthxide solvate, a tetrahydrofuran solvate, and an alcoholate such as a methanolate or ethanolate.

38. The method according to claim 37, wherein the polyoxornetalate is in the form of a hydrate containing between ½ and 500 molecules of water, preferably wherein the polyoxometalate is $H_5PV_2Mo_{10}O_{40}xnH_2O$ wherein n is 0 to 36.

* * * * *